United States Patent [19]
Vichroski et al.

[11] Patent Number: 5,437,867
[45] Date of Patent: Aug. 1, 1995

[54] SOLUBILIZING, THICKENING AND EMULSIFYING COSMETIC COMPOSITION AND PROCESS FOR PREPARATION OF SAME

[75] Inventors: Thomas J. Vichroski, Oakdale; Regina A. Costa, Port Jefferson Station; James A. Hayward, Port Jefferson, all of N.Y.

[73] Assignee: Collaborative Laboratories, East Setauket, N.Y.

[21] Appl. No.: 33,819

[22] Filed: Mar. 19, 1993

[51] Int. Cl.⁶ ............................................. A61K 9/10
[52] U.S. Cl. ................................. 424/401; 424/78.02; 514/937; 514/944
[58] Field of Search ........................... 424/401, 78.02; 514/944, 937

[56] References Cited

U.S. PATENT DOCUMENTS

| | | | |
|---|---|---|---|
| 4,297,098 | 10/1981 | Dasher et al. | 424/70.1 |
| 4,582,865 | 4/1986 | Balazs et al. | 524/29 |
| 4,708,861 | 11/1987 | Popescu et al. | 424/1.1 |
| 4,873,079 | 10/1989 | Hahn et al. | 424/70.6 |
| 4,999,348 | 3/1991 | Cioca et al. | 514/171 |

OTHER PUBLICATIONS

DeNavarre, "The Chemistry and Manufacture of Cosmetics," vol. IV, 1975, pp. 1067 and 1077.
"Carbopol® Water Soluble Resins," Service Bulletin GC-67, 1987, The BF Goodrich Company, Specialty Polymers Div., Cleveland, Ohio.
"CTFA Cosmetic Ingredient Dictionary," (4th Ed.), 1991, pp. 13, 80, 454, The Cosmetic, Toiletry & Fragrance Association, Inc.
"The Chemistry and Manufacture of Cosmetics," DeNavarre, Maison G., 1975, Continental Press, pp. 1029–1050 and 1063–1090 (2d Ed.).
"Formulating Superior Creams, Lotions, Solutions & Emulsions . . . " The Gattefosse Corporation, 1987.
"The Principles and Practice of Modern Cosmetics," Chemical Publishing Co., 1962, pp. 109, 110, 120.
"HYPAN® Hydrogels," Kingston Technologies, 1987.
"SANWET® Celanese Superabsorbent Materials," Hoechst Celanese Corporation, 1986.

*Primary Examiner*—Raj Bawa
*Attorney, Agent, or Firm*—Collard & Roe

[57] ABSTRACT

A cosmetic composition includes (a) ether alcohols conforming to the general formula $C_{(n)}H_{(2n+2)}O_{(n/2)}$, where n is an integer which ranges 4 to 12; (b) a homopolymer of acrylic acid cross-linked with an allyl ether of pentaerythritol or an allyl ether of sucrose, or copolymers of acrylic acid or acrylate derivative/acrylonitrile copolymers, or polyacrylic acid; (c) a fragrance oil or oils, or cosmetically acceptable oils or oily-type materials; and (d) water.

9 Claims, No Drawings

SOLUBILIZING, THICKENING AND EMULSIFYING COSMETIC COMPOSITION AND PROCESS FOR PREPARATION OF SAME

BACKGROUND OF THE INVENTION

1. Field of the Invention

The present invention relates to a series of novel cosmetic compositions for various uses containing a solubilizer, thickeners and emulsifying agents, and a process for their preparation. More particularly, the present invention relates to a cosmetic composition that allows for the preparation of cologne gels, colognes, skin perfumes, vitamin E gels, gels of other cosmetic ingredients, toilet water, etc. without the addition of volatile organic compounds (especially ethyl alcohol), and that can include the addition of a significant percentage of water, with a viscosity range at the high end ranging from that of a stiff gel down to that of a sprayable liquid at the low end of the viscosity range.

2. The Prior Art

Recently, the criteria for the commercial preparation of a fragrance product have become even more difficult. In addition to a finished product that feels elegant, adequately solubilizes the fragrance oil, is preferably clear and is safe to use, regulatory constraints now require a substantial reduction and the eventual elimination of the volatile organic compounds that have been traditionally used to achieve the desired product characteristics.

Prior art references related to cosmetic compositions are as follows.

The Balazs et al U.S. Pat. No. 4,582,865 is related to cross-linked gels of hyaluronic acid and products containing such gels.

The Popescu et al. U.S. Pat. No. 4,708,861 is related to liposome gel compositions.

The Cioca et al U.S. Pat. No. 4,999,348 is related to cosmetic and pharmaceutical compositions containing liquid crystals, and methods utilizing such compositions.

Other publications include:

1) Carbopol ® Water Soluble Resins, service Bulletin GC-67, 1987, The BF Goodrich Company, Specialty Polymers Division, Cleveland, Ohio 44131.

2) CTFA Cosmetic Ingredient Dictionary (Fourth Edition), 1991, The Cosmetic, Toiletry and Fragrance Association, Inc., Washington, D.C. 20036, pp. 13, 80, 454.

3) DeNavarre, Maison G., Vol. IV, The Chemistry and Manufacture of Cosmetics (Second Edition), 1975, Continental Press, Orlando, Fla. 32811, pp. 1029–1050 and 1063–1090.

4) Formulating Superior Creams, Lotions, Solutions & Emulsions: A Guide to Semi-Solid Product Development, 1987, The Gattefossé Corporation, Elmsford, N.Y. 10523.

5) Harry, Ralph G., The Principles and Practice of Modern Cosmetics, 1962, chemical Publishing Co., Inc., New York, N. Y. pp. 109, 110, 120.

6) Hypan ® Hydrogels, 1987, Kingston Technologies, Inc., Dayton, N.J.

7) Sanwet ® Celanese Superabsorbent Materials, 1986, Hoechst Celanese Corporation, Portsmouth, Va. 23703.

SUMMARY OF THE INVENTION

It is therefore an object of the present invention to provide a cosmetic composition, particularly a cosmetic fragrance product composition, and a process for its preparation, that eliminates the need for volatile organic compounds (particularly ethyl alcohol), allows for the inclusion of a significant proportion of water, adequately solubilizes most fragrance oils, maintains an elegant texture, can be made clear, easily tolerates extremely high levels of fragrance oils, is safe to use and relatively easy to manufacture.

Other objects and features of the present invention will become apparent when considered in combination with the following summary and detailed description of certain preferred embodiments and examples of the present invention.

The foregoing and related objects are achieved by providing a cosmetic composition containing:

a) an effective amount of ether alcohols having the general formula $C_{(n)}H_{(2n+2)}O_{(n/2)}$, where n is an integer which ranges from 4 to 12;

b) an effective amount of any of several commercially available homopolymers of acrylic acid cross-linked with an allyl ether of pentaerythritol or an allyl ether of sucrose, or any of several commercially available acrylic acid or acrylate derivative/acrylonitrile copolymers, or any of several commercially available starch grafted sodium polyacrylates, or polyacrylic acid;

c) an effective amount of a fragrance oil or other cosmetically acceptable oils or oily-type ingredients; and d) the balance up to 100% by weight of water based upon the total composition weight.

In addition, the composition may also contain an effective amount of any other suitable cosmetic ingredient, among which and specifically suited to the purpose are any of the many commercially available cosmetic raw materials intended to be used as co-solubilizers and triethanolamine or other similar-acting bases such as alkali metal hydroxides.

The cosmetic emulsion of the invention can optionally also comprise other ingredients as are conventionally employed in cosmetic products. Examples of other ingredients include perfumes, solubilizer, colorants such as staining dyes and pigments, humectants, germicides, sunscreens, vitamins and lipid materials.

Particularly preferred pigments, when present, include calcium oxide, barium oxide and aluminum oxide, iron oxides, titanium dioxide, and mica.

Particularly preferred humectants include butylene glycol, glycerol, sorbitol and other polyols.

Particularly preferred solubilizers include diethyl phthalate or octyldodecanol.

Particularly preferred germicides include Triclosan.

Particularly preferred vitamins include tocopherol acetate (vitamin E).

Particularly preferred sunscreens include octyl methoxycinnamate and butyl methoxydibenzolymethane.

Particularly preferred lipid materials include ceramides or lanolin wax.

An effective amount of the ether alcohol is preferably from 15% to 98.9% by weight, more preferably from to 90% by weight, and most preferably from 50.0% to 80.0% by weight, based upon the total composition weight.

An effective amount of the acrylic acid or acrylate polymer is preferably from 0.01% to 10% by weight, more preferably from 0.1% to 4% by weight, and most preferably from 0.6% to 3.3% by weight, based upon the total composition weight.

An effective amount of the fragrance is preferably from 0% to 60% by weight, more preferably from 3.0% to 40% by weight, most preferably from 8.0% to 28.0% by weight, based upon the total composition weight.

An effective amount of water is preferably from 0% to 60% by weight, more preferably from 0.5% to 30.0% by weight, most preferably from 1.5% to 20.0% by weight, based upon the total composition weight.

An effective amount of other suitable cosmetic ingredients is preferably from 0% to 20 by weight, more preferably from 5.0% to 15.0% by weight, most preferably from 9.0% to 12% by weight, based upon the total composition weight.

The cosmetic composition of the invention is useful as a cologne gel, a cologne, a vitamin E gel, gels of other oils or hydrophobes in general, a perfume cream, and a gel base.

The present invention will now be described in greater detail with reference being made to the following examples and preferred embodiments. It should, of course, be recognized that the following examples and preferred embodiments of the invention are intended solely for the purpose of illustration, and are not intended as limiting the scope thereof.

DETAILED DESCRIPTION OF PREFERRED EMBODIMENTS

In a preferred embodiment, the cosmetic composition of the present invention comprises:
a) about 15.0% to about 98.9% by weight of diethylene glycol monoethyl ether;
b) about 0.01% to about 10% by weight of a homopolymer of an acrylic acid cross-linked with an allyl ether of pentaerythritol or an allyl ether of sucrose;
c) 0% to about 60% by weight of a fragrance oil or fragrance oils;
d) 0% to about 60% by weight of water; and
e) 0% to about 20% by weight of other suitable cosmetic ingredients, and
with all weight percentages based upon the total composition weight.

The advantages of the present invention include the fact that the cosmetic composition of the invention has the unexpected ability to disperse the polymer in the ether alcohol, the development of a gel from this simple combination, and the ability to include water and other cosmetic ingredients without subsequently adversely affecting, within wide limits, the gelling, clarity characteristics or other desirable properties of the composition.

In a more preferred embodiment, the cosmetic composition of the present invention comprises:
a) about 30.0% to about 90.0% by weight of diethylene glycol monoethyl ether;
b) about 0.1% to about 4.0% by weight of a homopolymer of an acrylic acid cross-linked with an allyl ether of pentaerythritol or an allyl ether of sucrose;
c) 3.0% to about 40.0% by weight of a fragrance oil or fragrance oils;
d) 0.5% to about 30.0% by weight of water; and
e) 5.0% to about 15.0% by weight of other suitable cosmetic ingredients, and
with all weight percentages based upon the total composition weight.

In a most preferred embodiment, the cosmetic composition of this invention comprises:
a) about 50.0% to about 80.0% by weight of diethylene glycol monoethyl ether;
b) about 0 6to about 3 3by weight of a homopolymer of an acrylic acid cross-linked with an allyl ether of pentaerythritol or an allyl ether of sucrose;
c) 8.0% to about 28.0% by weight of a fragrance oil or fragrance oils;
d) 1.5% to about 20.0% by weight of water; and
e) 9.0% to about 12.0% by weight of other suitable cosmetic ingredients, and
with all weight percentages based upon the total composition weight.

The ingredients used in the composition of this invention should be of a quality or purity (such as U.S.P. of N.F.) suitable for cosmetic use and should be compatible when used together in a particular composition. Unless indicated otherwise, the physical properties of the components of the composition of the present invention specified herein are the properties of those components before they are mixed with the composition's other ingredients.

Among the commercially available suitable ether alcohols of the type that may be used in the present invention are those sold under the trademark TRANSCUTOL ® from the Gattefossé Corporation, Elmsford, N.Y. those sold under the trademark CARBITOL ® as a series of products from the Union Carbide Corporation, Tarrytown, N.Y. and those sold under the trademark CELLOSOLVE ® as a series of products, also from Union Carbide Corporation.

Among the commercially available suitable acrylic acid or acrylate polymers that may be used in the present invention are those sold under the trademark CARBOPOL ® as a series of products from B.F. Goodrich Company, Brecksville, Ohio; those sold under the trademark ACRITIMER ® as a series of products from the RITA Corporation, Crystal Lake, Ill. those sold under the trademark ACRISINT ® as a series of products from 3V-Sigma, Weehawken, N.J. those sold under the trademark THIXOL ® 100-C from Coatex, Caluire, France; those sold under the trademark HYPAN ® as a series of products from Kingston Hydrogels, LP, Dayton, N.J. those sold under the trademark ACRYSOL ® ASE-75 from Rohm & Haas Company, Inc., or sold under the trademark ACUMER ®1510 from Rohm & Haas Company, Inc., Philadelphia, Pa. those sold under the trademark SANWET ® as a series of starch grafted sodium polyacrylates from Hoechst Celanese Corporation, Portsmouth, Virginia; and those sold under the trademark HOE S 3915 ® from Hoechst Aktiengesellschaft Frankfurt am Main, Germany.

The composition of the present invention may be prepared by the following process steps, which are carried out at room temperature (25° C.) and under one atmosphere of pressure
a) Use of a marine or propeller type mixer to disperse the acrylic acid or acrylate polymer in a portion of the total amount of ether alcohol present in the composition will produce a preproduct. In this first embodiment, the mixing occurred at 500 to 1500 rpm and lasted for 15 to 30 minutes. Dispersing the acrylic acid or acrylate polymer in all of the total amount of ether alcohol present in the composition can also be carried out with the marine type mixer. In this second embodiment, the mixing occurred at 500 to 1500 rpm and lasted for 15 to 30 minutes. Concentrations of at least as high as 10% by weight polymers are possible by changing to side-wiping planetary type mixing at 10 to 50 rpm for 5 to 15 minutes once all the polymer particles have been wetted out and continuing to mix until the dispersion is uniform. The weight percent of the polymers, or other ingredients, is based upon the total composition weight.

b) If this dispersion contains more polymer than the final product requires, as in the first embodiment preproduct, it may then be diluted and mixed until uniform with the remaining ether alcohol.

c) The fragrance oil of the final product is then added and mixed until smooth and uniform.

d) Any other components that are soluble in the ether alcohol are added and mixed until smooth and uniform.

e) The water and any water-soluble ingredients, except bases such as triethanolamine or alkali metal hydroxides, are added and mixed until uniform.

f) Finally, any necessary bases such as triethanolamine or alkali metal hydroxides are added and mixed until uniform. Such bases may be diluted in any suitable portion of water so as not to cause localized precipitation of the polymer upon the addition of the base.

The above procedure is generic to all of the specific types of compositions and may be modified as necessary to achieve the preparation of a specific final product. Different fragrance oils may require different orders of addition, particularly of the water and any necessary base such as triethanolamine or alkali metal hydroxide, to achieve the finished product. The use of a predispersed ether alcohol/polymer mixture preproduct with the polymer at a significantly higher concentration level in the pre-dispersion than that required in the final formulation is a particularly advantageous method embodiment. This is because the incorporation at an early stage in the process of most of the other components of the product prevents uniform dispersion of the polymer and subsequently causes premature gelling of the polymer.

The following non-limiting examples further illustrate the present invention:

EXAMPLES

Example 1 (Cologne Gel)

| Ingredient | Parts by Weight |
| --- | --- |
| Ethoxydiglycol | 72.75 |
| Acrylate polymer sold under the trademark CARBOPOL ® 980 (B.F. Goodrich) | 2.25 |
| Fragrance Oil | 15.00 |
| Water | 10.00 |
| | 100.00 |

The above ingredients were mixed and processed in the following manner. At room temperature, the ethoxydiglycol was placed in a suitably sized container. A propeller (marine) type mixer was placed in the container and rapid mixing occurred at approximately 1100 rpm so that the ethyoxydiglycol started to form a vortex. The acrylate polymer CARBOPOL ®980 was sprinkled into the vortex. When all of the acrylate polymer CARBOPOL ®980 had been sprinkled in and wetted by the ethoxydiglycol, the mixer was slowed to approximately 700 rpm to eliminate the vortex. The mixing was continued until the batch was smooth and uniform with no lumps of undispersed CARBOPOL ®980. The remaining ingredients were then added in the order listed,.and each ingredient was mixed for about 15 minutes until uniformly dispersed before the next ingredient was added. The resulting product was in the form of a clear gel and had a viscosity of about 30,080 centipoise.

This final product was topically applied to the skin of the forearm of an adult human male. After two hours, the final product was found to be, and continued to be, a safe, nonirritating, and effectively useful cologne gel.

Example 2 (Cologne)

| Ingredient | Parts by Weight |
| --- | --- |
| A. Preproduct | |
| Ethoxydiglycol | 26.6265 |
| Acrylate polymer sold under the trademark CARBOPOL ® 980 (B.F. Goodrich) | 0.8235 |
| B. Final Product | |
| Preproduct A | |
| Ethoxydiglycol | 36.6761 |
| PPG-2-Isoceteth-20 Acetate sold under the trademark CUPL ® PIC(Heterene, Inc., Paterson, New Jersey) | 0.1180 |
| PPG-2-Isodeceth-12 sold under the trademark SANDOXYLATE ® SX424 (Sandoz Chemicals, Charlotte, NC) | 0.1180 |
| Butylene Glycol | 3.9254 |
| Fragrance oil | 23.5875 |
| Water | 1.8750 |
| Diethyl Phthalate | 6.2500 |
| | 100.0000 |

The above ingredients were mixed and processed as follows. The ethoxydiglycol at room temperature of preproduct A (Phase A) was placed in a suitably sized container. A propeller (marine) type mixer was placed in the container and rapid mixing occurred at approximately 1100 rpm until the ethoxydiglycol started to form a vortex. The acrylate polymer CARBOPOL ®980 was sprinkled into the vortex. When all of the acrylate polymer CARBOPOL ®980 had been sprinkled in and wetted by the ethoxydiglycol, the mixer was slowed to approximately 700 rpm to eliminate the vortex. The mixing was continued until the preproduct batch was smooth and uniform, with no undispersed lumps of acrylate polymer CARBOPOL ®980. The ingredients of Phase B were then added in the order listed, and each ingredient was mixed for about 15 minutes until uniformly dispersed before the next ingredient was added. The resulting final product was in the form of a clear, sprayable liquid with a viscosity of about 150 centipoise.

This final product was topically applied to the skin of a forearm of an adult human male. After three hours, the final product was found to be, and continued to be, a safe, nonirritating and effectively useful cologne°

Example 3 (Cologne Gel)

| Ingredient | Parts by Weight |
| --- | --- |
| A. Preproduct | |
| Ethoxydiglycol | 61.3800 |
| Acrylate polymer sold under the trademark CARBOPOL ® 980 (B.F. Goodrich) | 2.2500 |
| B. Final Product | |
| Preproduct A | |
| PPG-2-Isoceteth-20 Acetate sold under the trademark CUPL ® PIC (Heterene, Inc., Paterson, NJ) | 0.3225 |
| PPG-2-Isodeceth-12 sold under the trademark | 0.3225 |

-continued

| Ingredient | Parts by Weight |
|---|---|
| SANDOXYLATE ® SX424 (Sandoz Chemicals, Charlotte, NC) | |
| Butylene Glycol | 10.7250 |
| Fragrance oil | 10.0000 |
| Water | 15.0000 |
| | 100.0000 |

The above ingredients were mixed and processed in a manner analogous to that described in Example 2 above, with the exception that side-wiping mixing at approximately 17 rpm for 10 minutes was added to the processing when necessary as the viscosity built up. The resulting final product was in the form of a clear gel with a viscosity of about 223,100 centipoise.

This final product was topically applied to the skin of the forearm of an adult human male. After two hours, the final product was found to be, and continued to be, a safe, nonirritating and effectively useful cologne gel.

Example 4 (Vitamin E Gel)

| Ingredient | Parts by Weight |
|---|---|
| A. Preproduct | |
| Ethoxydiglycol | 70.2678 |
| Acrylate polymer sold under the trademark CARBOPOL ® 980 (B.F. Goodrich) | 2.5758 |
| B. Final Product | |
| Preproduct A | |
| PPG-2-Isoceteth-20 Acetate sold under the trademark CUPL ® PIC (Heterene, Inc., Paterson, NJ) | 0.3692 |
| PPG-2-Isodeceth-1 sold under the trademark SANDOXYLATE ® SX424 (Sandoz Chemicals, Charlotte, NC) | 0.3692 |
| Butylene Glycol | 12.2780 |
| Tocopherol Acetate (Vitamin E) | 6.9600 |
| Water | 4.9500 |
| Diethyl Phthalate | 2.2300 |
| | 100.0000 |

The above ingredients were mixed and processed in a manner analogous to that described in Example 2 above, including preparing the pre-product pre-dispersion of polymer in ether alcohol by combining the first two ingredients separately (Preproduct Phase A). The resulting final product was in the form of a clear gel with a viscosity of about 65,300 centipoise and is an example of a non-fragrance product.

This final product was topically applied onto the skin of the forearm of an adult human male. After three hours, the final product was found to be, and continued to be, a safe, nonirritating and effectively useful vitamin E gel.

Example 5 (Perfume Cream)

| Ingredient | Parts by Weight |
|---|---|
| A. Preproduct | |
| Ethoxydiglycol | 15.52 |
| Acrylate polymer sold under the trademark CARBOPOL ® 980 (B.F. Goodrich) | 0.48 |
| B. Final Product | |
| Preproduct A | |
| Fragrance Oil | 7.50 |
| Water | 76.08 |
| Triethanolamine | 0.42 |

-continued

| Ingredient | Parts by Weight |
|---|---|
| | 100.00 |

The above ingredients were mixed and processed in a manner analogous to that described in Example 2 above, including preparing the pre-product pre-dispersion of the polymer in ether alcohol by combining the first two ingredients separately (Preproduct A). The resulting final product was in the form of an opaque cream emulsion and had a viscosity of about 359,500 centipoise.

This final product was topically applied to the skin of the forearm of an adult human male. After three hours, the final product was found to be, and continued to be, a safe, nonirritating, and effectively useful perfume cream.

Example 6 (Gel Base)

| Ingredient | Parts by Weight |
|---|---|
| A. Preproduct | |
| Ethoxydiglycol | 48.50 |
| Acrylate polymer sold under the trademark CARBOPOL ® 980 (B.F. Goodrich) | 1.50 |
| B. Final Product | |
| Preproduct A | |
| Water | 49.25 |
| Triethanolamine | 0.75 |
| | 100.00 |

The above ingredients were mixed and processed in a manner analogous to that described in Example 2 above, including preparing the pre-product pre-dispersion of the polymer in ether alcohol by combining the first two ingredients separately (Preproduct Phase A). The resulting final product was in the form of a clear gel with a viscosity of about 445,100 centipoise.

This final product was topically applied to the skin of the forearm of an adult human male. After three hours, the final product was found to be, and continued to be, a safe, nonirritating and effectively useful gel base.

While several embodiments of the present invention have been shown and described, it is to be understood that many changes and modifications may be made thereunto without departing from the spirit and scope of the invention as defined in the appended claims.

What is claimed is:

1. A cosmetic composition comprising:
   (a) about 15.0% to about 98.9% by weight of ether alcohols having the formula $C_{(n)}H_{(2n+2)}O_{(n/2)}$, where n is an integer which ranges from 4 to 12;
   0.01% to about 10% by weight of a homopolymer of acrylic acid cross-linked with an allyl ether of pentaerythritol;
   (c) 0% to about 60.0% by weight of a fragrance oil; and
   (d) the balance up to 100% by weight of water; with all weight percents based upon the total composition weight.

2. A cosmetic composition comprising:
   (a) about 15.0% to about 98.9% by weight of diethylene glycol monoethyl ether;
   (b) 0.01% to about 10% by weight of a homopolymer of an acrylic acid cross-linked with an allyl ether of pentaerythritol;
   (c) 0% to about 60.0% by weight of a fragrance oil;

(d) 0% to about 60.0% by weight of water;
(e) 0% to about 20.0% by weight of other cosmetic ingredients; and
with all weight percents based upon the total composition weight.

3. A cosmetic composition comprising:
(a) about 30.0% to about 90.0% by weight of diethylene glycol monoethyl ether;
(b) about 0.1% to about 4.0% by weight of a homopolymer of an acrylic acid cross-linked with an allyl ether of pentaerythritol;
(c) 3.0% to about 40.0% by weight of a fragrance oil;
(d) 0.5% to about 30.0% by weight of water;
(e) 5.0% to about 15.0% by weight of other cosmetic ingredients; and
with all weight percents based upon the total composition weight.

4. A cosmetic composition comprising:
(a) about 50.0% to about 80.0% by weight of diethylene glycol monoethyl ether;
(b) about 0.6% to about 3.3% by weight of a homopolymer of an acrylic acid cross-linked with an allyl ether of pentaerythritol;
(c) 8.0% to about 28.0% by weight of a fragrance oil;
(d) 1.5% to about 20% by weight of water;
(e) 9.0% to about 12.0% by weight of other cosmetic ingredients; and
with all weight percents based upon the total composition weight.

5. A process for the preparation of a cosmetic composition containing
(1) a total amount of an ether alcohol utilizable either in a portion thereof or in all of the total amount thereof;
said ether alcohol having the formula $C_{(n)}H_{2n+2}O_{(n/2)}$ where n is an integer which ranges from 4 to 12; with there being about 15.0% to about 98.9% y weight of said ether alcohol;
(2) 0.01% to about 10% by weight of a homopolymer of an acrylic acid cross-linked with an allyl ether of pentaerythritol;
(3) 0% to about 60.0% by weight of a fragrance oil;
(4) 0% to about 60.0% by weight of water; and
(5) 0% to about 20.0 by weight of other cosmetic ingredients,
with all weight percents based upon the total composition weight
comprising the steps of
(a) dispersing by mixing said acrylic acid homopolymer in a portion of the total amount of ether alcohol present in the composition to produce a preproduct, and having remaining ether alcohol; or dispersing the acrylic acid homopolymer in all of the total amount of ether alcohol present in the composition to produce a dispersion;
(b) if said dispersion contains said preproduct, then diluting and mixing the preproduct until uniform with the remaining ether alcohol;
(c) adding fragrance oil and mixing until smooth and uniform;
(d) adding any other components that are soluble in the ether alcohol and mixing until smooth and uniform;
(e) adding water and any water-soluble ingredients, except bases, and mixing until uniform;
(f) adding any necessary bases and mixing until uniform to produce said cosmetic composition as a final product.

6. The process according to claim 5, wherein a preproduct is first prepared, and then subsequently the final product is produced.

7. The process according to claim 5, wherein the final product is produced without the preparation of a preproduct.

8. The process according to claim 5, wherein the cosmetic composition contains:
(1) about 30.0% to about 99.0% by weight of said ether alcohol having the formula $C_{(n)}H_{(2n+/2)}O_{(n/2)}$, where n is an integer which ranges from 4 to 12;
(2) about 0.1.% to about 4.0.% by weight of said homopolymer of acrylic acid cross-linked with an allyl ether of pentaerythritol;
(3) 3.0% to about 40.0% by weight of said fragrance oil;
(4) 0.5% to about 30% by weight of water; and
(5) 5.0% to about 15.0% by weight of other cosmetic ingredients;
with all weight percents based upon the total composition weight.

9. The process according to claim 8, wherein said ether alcohol is diethylene glycol monoethyl ether.

* * * * *